United States Patent

Shakespeare

Patent Number: 6,111,651
Date of Patent: Aug. 29, 2000

[54] METHOD AND APPARATUS FOR MEASURING PROPERTIES OF A MOVING WEB

[75] Inventor: John Shakespeare, Siuro, Finland

[73] Assignee: Neles Paper Automation Oy, Helsinki, Finland

[21] Appl. No.: 09/116,268

[22] Filed: Jul. 16, 1998

[51] Int. Cl.[7] ................................................. G01N 21/84
[52] U.S. Cl. ............................................. 356/429; 356/431
[58] Field of Search ................................... 356/421, 422, 356/424, 402, 429, 431, 364, 238.1, 238.2

[56] References Cited

U.S. PATENT DOCUMENTS 5,400,258  3/1995  He ............................................... 356/431
5,492,601  2/1996  Ostermayer et al. ...................... 356/426

*Primary Examiner*—Frank G. Font
*Assistant Examiner*—Roy M. Punnoose
*Attorney, Agent, or Firm*—Ladas & Parry

[57] ABSTRACT

The invention relates to a method and apparatus for measuring properties of a moving web. A stimulus is directed onto the moving web by an excitation element and the effect of the web on the stimulus is measured with a detection element. At the measuring point the web is supported by a measurement support sheet. The measurement support sheet comprises at least two regions having different but known responsiveness to one or more forms of stimulus or causing different but known transformation to one or more forms of stimulus.

20 Claims, 1 Drawing Sheet

METHOD AND APPARATUS FOR MEASURING PROPERTIES OF A MOVING WEB

BACKGROUND OF THE INVENTION

The invention relates to a method for measuring properties of a moving web, the method comprising applying a stimulus to the web and measuring the effect of the web on the stimulus, the web being supported by a sheet at the measuring point.

The invention further relates to an apparatus for measuring properties of a moving web, the apparatus comprising at least one excitation element for applying a stimulus to the web and at least one detection element for detecting the radiation transformed by the web and at least one sheet for supporting the web at the measuring point.

Properties of a moving web are usually measured by means of a traversing measuring frame. For many measurements, for example color and basis weight measurements, the web needs to be unsupported in prior art solutions. For example in color measurements the means of measurement requires a specific reference material opposite the sensor.

When using reflection measurement on a supported web, the measurement contains both emissions reflected by the web and emissions which were transmitted through the web, reflected by the support sheet, and transmitted back through the web. Since the web is opaque only to certain emissions, the reflection from the support sheet might cause a significant and variable bias to the measurement.

In bulky measurement devices and especially in devices which traverse the web or in apparatuses containing plural devices deployed across the web, the path length over which the web is unsupported may be significant. Stresses on the web generally increase rapidly with the increase of speed of conveyance or processing. Thus the unsupported sections can limit the speed of processing the web, since there is a maximum stress the web can bear. Moreover, since properties of a web normally exhibit some variation, the maximum bearable stress may vary. This leads to a greater incidence of interruptions to production caused by web breaks in the unsupported sections. The measuring frame itself and its measuring carriages are also harmful in a fast machine since the gap between the upper and lower parts of the carriage is very small, and in order to avoid marks the sheet should not touch the carriages. An unsupported web may also flap, and if it then goes between the measuring carriages, it is highly probable that this will cause marks, or even holes, to the sheet.

SUMMARY OF THE INVENTION

The object of the present invention is to provide a method and an apparatus which allow measurement of properties of a web accurately and reliably as well as to avoid the above-mentioned disadvantages.

The method of the invention is characterized in that the web is supported by a moving measurement support sheet at the measuring point, the measurement support sheet comprising at least two regions having different but known responsiveness to one or more forms of stimulus or causing different but known transformation to one or more forms of stimulus.

The apparatus of the invention is characterized in that the apparatus comprises a moving support sheet which is arranged to support the web at the measuring point, the support sheet comprising at least two regions having different but known responsiveness to one or more forms of stimulus or causing different but known transformation to one or more forms of stimulus.

The essential idea of the invention is that properties of a moving web which is supported by a sheet are measured, the support sheet comprising at least two regions having different but known responsiveness to one or more forms of stimulus or causing different but known transformations to one or more forms of stimulus. The idea of a preferred embodiment is that the support sheet comprises at least one region that is perfectly absorptive or otherwise perfectly non-reflective to the excitation stimulus. The idea of a second preferred embodiment is that the support sheet comprises at least one region that is perfectly non-absorptive or otherwise perfectly reflective to the excitation stimulus. The idea of a third preferred embodiment is that the support sheet comprises at least one region which approximates an ideal white and at least one region which approximates an ideal black for a range of electromagnetic wavelengths. Preferably, the support sheet moves in substantially non-slipping contact with the web.

An advantage of the invention is that because the web is supported, the stresses of movement and stresses exerted during processing operations are shared between the web and the support sheet. Thus the conveying and processing of the web may be carried out at higher speed than an unsupported web could sustain. Moreover, interruptions to processing due to web breaks in unsupported sections will be less likely and less frequent. When at least one region of the support sheet approximates for example an ideal black, the water between the support sheet and the means of measurement can be measured by measuring the backscatter of suitably chosen infrared radiances. When the support sheet contains some regions which are reflective in a range of electromagnetic wavelengths in which the web is known to be substantially opaque and non-reflective and by using one or more excitation elements emitting said wavelengths and one or more detectors responsive to said wavelengths, holes in the web can be observed and measured over said regions of the support sheet.

When the support sheet contains some regions which approximate an ideal white for a range of electromagnetic wavelengths for which the web is partially opaque and some regions which approximate an ideal white for the same range of wavelengths, the contrast of the sheet can be measured with black and white backings and hence the opacity of the sheet can be calculated. A second advantage of this embodiment is that spectrophotometric measurements of the unsupported surface of the web over the black regions and over the white regions of the support sheet can be used to calculate the translucence of the web. A third advantage of this embodiment is that the properties of an effectively opaque pad made from many thicknesses of the web can be calculated from the same spectrophotometric measurements. In prior art these measurements would require transmission measurement and backscatter or reflection measurements made with an unsupported web. Spectrophotometric measurements of this type in the visible wavelengths allow color to be measured, while measurements in other wavelength ranges allow other properties of the sheet to be determined.

The above mentioned electromagnetic and photometric measurements, when made on the web above two regions of the support sheet with different known reflectivity, can be used to claculate several properties of the web at each measured wavelength. The opacity, reflectance, transluscence, etc. of a single layer or plural layers of the web, or of a pad of arbitrary thickness made from the web can be calculated using a multi-flux model, or a four-flux, two-flux, or Kulbelka-Munk model. In each case, the calculation may be of said properties when an arbitrary material of known properties is used as a backing for said layer, layers, or pad. The various equations and methods of multi-flux models, including four-flux, two-flux, and Kubelka-Munk models are well-known per se, and are not further discussed here being described in Völz, H. G., "Industrial Color Testing", VCH, Weinheim Germany, 1995, among others.

Measurements made by illuminating the web with polarized infra-red light where the support sheet contains at least one region which is reflective and at least one region which is non-reflective to that range of wavelengths may be used to determine the fiber orientation distribution of the web. Equivalently, the illumination can employ unpolarized light, and the detector can distinguish between the different planes of polarization in the reflected light. The measurement of the fiber orientation is accomplished by detecting the difference in the amount of infra-red light reflected from the two regions of the support sheet through the web and by changing the plane of polarization. The polarization angle for maximum difference in reflection between the regions corresponds to the dominant fiber orientation angle, and the ratio of the maximum and minimum differences in reflected light correlates with the fiber orientation index.

BRIEF DESCRIPTION OF THE DRAWINGS

The invention will be described in greater detail in the accompanying drawing in which.

DESCRIPTION OF EMBODIMENTS

Figure 1:
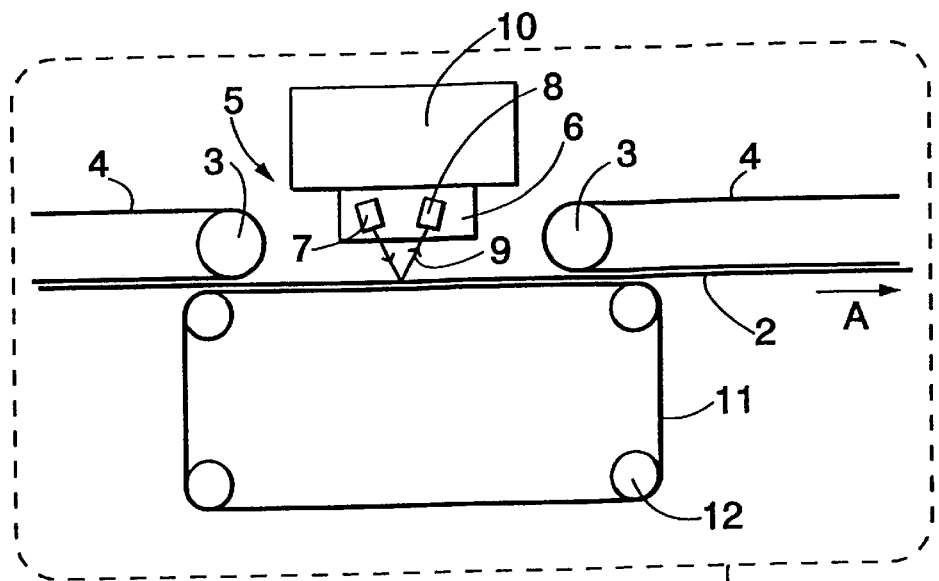
FIG. 1 is a schematic side view of the solution of the invention.

FIG. 1 schematically illustrates, by means of broken lines, a paper or board machine 1 in connection with which the arrangement of the invention is to be used. The web 2 to be measured moves in the direction of arrow A and is supported and guided by guide rolls 3 and guide or process support sheets 4. There is a measurement unit 5 arranged to measure properties of the web 2. The measurement unit 5 comprises a measuring device 6. The measuring device 6 comprises an excitation element 7 which emits radiation 9 which a detection element 8 detects. The measuring device 6 is arranged to a measuring frame 10 where the measuring device 6 may traverse in a direction transverse to the direction A of the web 2. At the measuring point the web 2 to be measured is supported by a measurement support sheet 11, which is arranged to turn by means of guide rolls 12. The web 2 is essentially all the time supported either by a process support sheet 4 or by a measurement support sheet 11, with no open unsupported sections.

The excitation element 7 continuously or intermittently directs radiation 9 or a first stimulus onto the unsupported surface of the web 2. The form of the stimulus may be for example x-ray, uv, visible, ir, rf, magnetic or electrostatic field, acoustic, etc. Further, the quality of the stimulus may be for example polarized, monochrome, coherent, having a particular spectral distribution etc. Also, the stimulus may be for example pulsed, continuous, cycling through different intensities, frequency modulated, etc. The detection element 8 is responsive to the first stimulus of the excitation element 7 or responsive to a second stimulus into which said first stimulus may be transformed as a consequence of properties of the web 2 or measurement support sheet 11. The form of the detected stimulus may be for example the same as that of excitation, or transformation of the excitation such as changed in polarity or wavelength, dispersed or scattered, transmuted, etc. Further, the relative geometry of the excitation element 7 and the detection element 8 may vary. The options are for example incident angle, excident angle, rotation between incident and excident angles, directional versus diffuse, uni-directional versus rotary versus annular, etc. The properties calculated from the measurements may be for example moisture, fiber orientation, gloss, shrinkage, color, ash content, etc.

Figure 2:
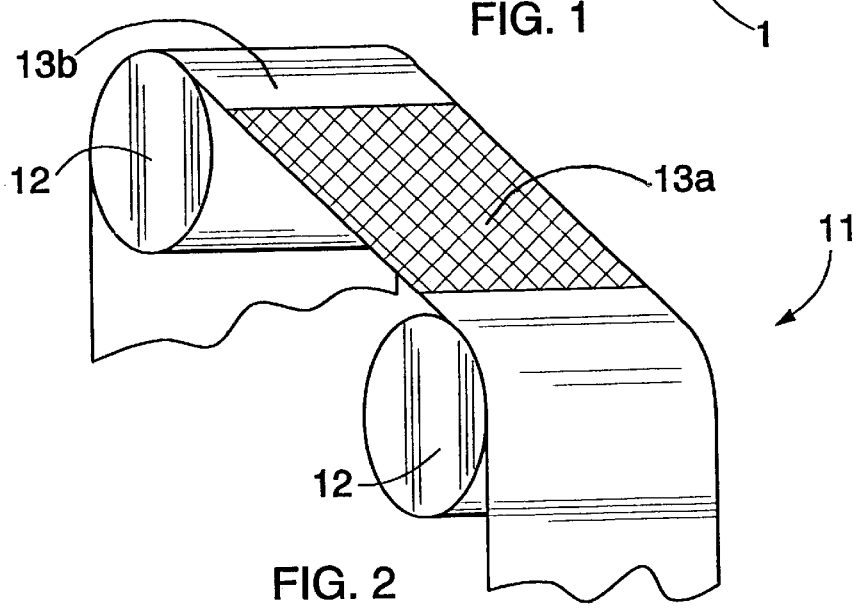
FIG. 2 is a schematic and axonometric view of a support sheet of the invention.

FIG. 2 illustrates a measurement support sheet 11. The measurement support sheet 11 comprises regions 13a and 13b, which have different known properties so that the properties of the web 2 may be measured accurately. The properties required of the different regions 13a and 13b of the measurement support sheet 11 are determined by the means of excitation 7 used in each of one or more means 6 of measuring properties of the web 2.

If a region 13a or 13b of the measurement support sheet 11 is perfectly absorptive or otherwise perfectly non-reflective to the excitation emissions including said emissions as transformed by transmission through the web 2, then its effect on backscatter or reflection measurement techniques is negligible.

If a region 13a or 13b of the measurement support sheet 11 is perfectly non-absorptive or otherwise perfectly reflective to the excitation emissions, then it affects backscatter or reflection measurement of a property which is normally measured by transmission measurement so that the apparent thickness and mass of the web 2 double. Depending on the geometrical relation between the excitation element 7 and the detection element 8 the backing may need to be either diffusely reflective or specularly reflective to said emissions.

In practice, the regions 13a and 13b of the measurement support sheet need only be differently reflective or differently absorptive to the excitation emissions, and need not be perfectly absorptive or reflective. The contrast between the regions 13a and 13b for the excitation emissions is one of the factors determining the ease with which properties of the web may be measured. In practice, there may be more than two regions on the measurement support sheet, and some regions may present an absorptivity or reflectivity which is intermediate in value between that of other regions. For example, there may be six regions, two of 90% reflectivity, two of 10% reflectivity, and one each of 30% and 70% reflectivity.

In this invention the measurement support sheet 11 for a moving web 2 is so constructed as to enhance the mensuration of certain properties of the web 2, while it is supported. In particular, measurement of properties by means of an excitation element 7 and detection element 8 both on the unsupported side of the web 2 are enhanced. The enhancement allows some properties to be measured in this way, which would commonly be measured with an excitation element 7 and a detection element 8 on the opposite side of an unsupported web 2.

The measurement support sheet 11 may reflect back some of the emissions, which have been transmitted through the web. The emissions may have been modulated or transformed in reflection by the measurement support sheet 11 as well as in passing through the web 2 before and after reflection by the measurement support sheet 11.

In practice neither a perfectly absorptive nor a perfectly reflective measurement support sheet 11 is attainable. However, regions 13a and 13b which have nearly perfect absorptive and nearly perfect reflective properties are attainable. For example surfaces with diffuse reflectance factor of nearly 100% in all wavelengths of the visible range, in other words ideal white, or which have specular reflectance factor of nearly 100% in all wavelengths of the visible range, in other words ideal mirror, or which have reflectance factors of nearly zero in all wavelengths of the visible range, in other words ideal black, are readily available. The measurement support sheet 11 may be made of different materials or some sections of it may be coated for example with a layer of black fabric and others with a layer of white fabric. The reflective region may be provided for example by using barium sulphate and the black region for example by using carbon black.

Regions 13a and 13b advantageously extend from one edge of the measurement support sheet 11 to the other in the cross direction. The properties of the region 13a or 13b should be substantially uniform throughout the region.

The examples in the above discussion employed differences in diffuse reflectiveness, specular reflectiveness and absorption in certain electromagnetic wavelength ranges. Additionally or alternatively to these properties many other properties may differ between regions 13a and 13b of the measurement support sheet 11. For example reflectiveness in some regions of the measurement support sheet 11 may differ between planes of polarization or regions 13a and 13b may differ in fluorescence characteristics or in microwave resonance characteristics, or in electrical conductivity. The desired properties in each region can usually be achieved by constructing that part of the support sheet from a suitable material, or by combining a suitable material into the material of that region of the support sheet. For example, a region of high electrical conductivity can be achieved by using aluminized fibers in the sheet, or by bonding aluminium foil to the surface of the sheet.

In one embodiment of this invention the measurement support sheet contains some regions 13a which approximate an ideal black in a range of infra-red wavelengths. One advantage of this embodiment is that the water between the support sheet and the means of backscatter measurement can be measured by measuring the backscatter of suitably chosen infra-red radiances.

In another embodiment of this invention the measurement support sheet 11 contains some regions 13b which approximate an ideal white and some regions 13a which approximate an ideal black for a range of wavelengths. The web is illuminated with electromagnetic radiation in said range of wavelengths and the reflected light is measured at several wavelengths in that range. One advantage of this embodiment is that the contrast of the sheet can be measured with the black and white backings and hence the opacity of the sheet at each measured wavelength can be calculated. A second advantage of this embodiment is that spectrophotometric measurements of the electromagnetic radiation reflected from the unsupported surface of the web over the black regions 13a and over the white regions 13b of the measurement support sheet 11 can be used to calculate the translucence of the web 2. A third advantage of this embodiment is that the reflectance spectrum of an effectively opaque pad made from many thicknesses of the web 2 can be calculated from the same spectrophotometric measurements. In prior art these measurements would require transmission measurement and reflection measurements made with an unsupported sheet. In the case that the above mentioned electromagnetic radiation is light in the visible band, the measurements are of the opacity, transluscent color and reflective color of a single sheet, and of the reflective color of an opaque pad, including effects of visual fluorescence. In the case that the electromagnetic radiation is in the infra-red range of wavelengths, then the measurements are of the absorption spectrum of the web, and hence of the amounts or proportions of various constituents in the material of the web. This qualitative or quantitative analysis may be performed using chemometric or other statistical techniques in conjunction with a set of known spectra or calibration data. Chemometric methods are well-known per se, and advances in the field are published in the Journal of Cheometrics (Wiley). For example, chemometric use of the partial-least-squares method is described in Höskuldsson, a. "PLS Regression Methods", Journal of Chemometrics, volume 2, pages 211–228, 1988. Other suitable statistical methods are described in Basilevsky, A., "Statistical Factor Analysis and Related Methods", Wiley, N.Y., 1994, among others.

In yet another embodiment of this invention the measurement support sheet 11 contains some regions 13a or 13b which are reflective in a range of wavelengths in which the web is known to be substantially opaque. By use of one or more excitation elements 7 emitting said wavelengths and one or more detection elements 8 responsive to said wavelengths, holes in the web 2 can be observed and measured over said regions 13a and 13b of the measurement support sheet 11.

In a further embodiment of this invention, the support sheet contains regions which are differently reflective to a range of infra-red wavelengths. By illuminating the web with polarized infra-red light and by detecting the amount of said light reflected with different planes of polarization over the two regions, the dominant fiber orientation direction and the degree of orientation can be measured. Equivalently, the illumination can be with unpolarized infra-red light, and the detection of reflected light can discriminate between different polarization planes.

In yet a further embodiment of this invention, the support sheet contains at least one region which has a high electrical conductivity, and electromagnetic radiation at one or more microwave wavelength bands is directed through the web and the reflection from the support sheet is detected with a confocal resonator. The moisture content of the web is measured from the imaginary part of the web permittivity, and its thickness from the real part.

Since different stimuli are used to measure different properties, the measurement support sheet 11 would need to have a number of regions 13a and 13b to provide contrast for each stimulus. A synchronization input might be required for the measurement device so it knows which support band is currently underneath. Alternatively such synchronization could be provided by one region 13a or 13b on the measurement support sheet 11, if the region is directly detectable to one of the measurement devices, for example if it is luminescent in a particular IR-band.

Figure 3:
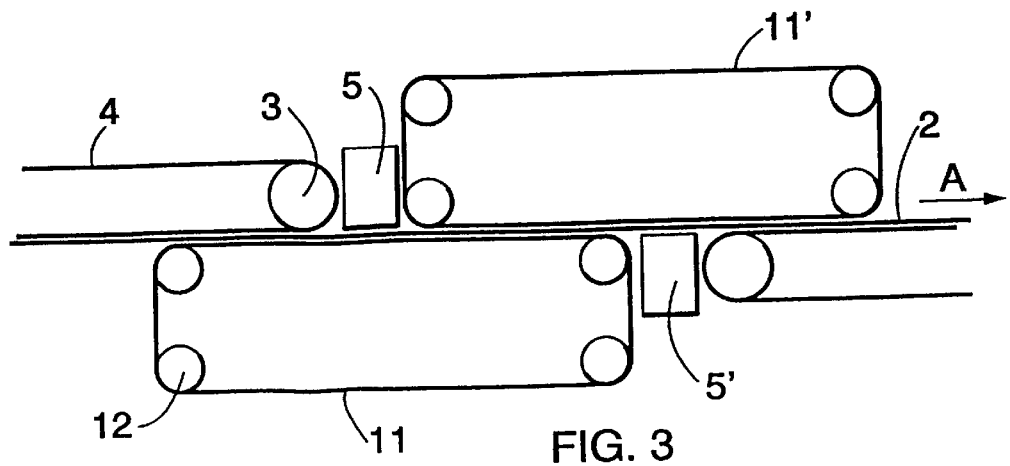
FIG. 3 is a schematic side view of another embodiment of the invention.

FIG. 3 shows an embodiment where measurements are made on both sides of the web 2. A first measurement unit 5 measures the first side of the web 2 and at the first measurement unit 5 the web 2 is supported by a first measurement support sheet 11. A second measurement unit 5' is arranged to measure the second side of the web 2. At the second measurement unit 5' the web 2 is supported by a second measurement support sheet 11'. The second measurement unit 5' and second measurement support sheet 11' need not be similar to the first measurement unit 5 and first measurement support sheet 11.

This invention contemplates and encompasses measurement using a measurement unit 6 comprising a stationary arrangement of sensors located at a single position above the moving supported web or comprising plural stationary arrangements of sensors deployed at different locations across the moving supported web. It further contemplates and encompasses using a measurement unit 5 comprising a moving arrangement of sensors which traverses across the moving supported web, or comprising a scanning or imaging arrangement of sensors which measures substantially the whole width of the moving supported web. It also contemplates and encompasses measurement using a measurement unit 5 comprising plural arrangements of sensors, such as stationary, traversing, scanning, etc., which are independently operated.

The drawing and the related description are only intended to illustrate the inventive idea. The details of the invention may vary within the scope of the claims. Thus the measurement support sheet 11 could also function as a process support sheet. Moreover, while a point on the support sheet may be in a region 13a or 13b with respect to a first stimulus such as visible light, it may also be in a region 13a' or 13b' with respect to a second stimulus such as microwave radiation. The regions 13a' and 13b' for the second stimulus need not correspond in size, shape, or location with the regions 13a and 13b for the first stimulus Each of the regions 13a' and 13b' may overlap fully or in part, or be entirely separate from regions 13a and 13b.

What is claimed is:

1. A method for measuring properties of a moving web, the method comprising directing a stimulus on the web and measuring the effect of the web on the stimulus, the web being supported by a moving measurement support sheet at the measuring point, the measurement support sheet comprising at least two regions having different but known responsiveness to one or more forms of stimulus or causing different but known transformation to one or more forms of stimulus.

2. A method according to claim 1, wherein the measurement support sheet comprises at least one region that is essentially completely absorptive or otherwise essentially non-reflective to the excitation stimulus.

3. A method according to claim 1, wherein the measurement support sheet comprises at least one region that is essentially non-absorptive or otherwise essentially completely reflective to the excitation stimulus.

4. A method according to claim 2, wherein the measurement support sheet comprises at least one region that is essentially non-absorptive or otherwise essentially completely reflective to the excitation stimulus.

5. A method according to claim 1, wherein the measurement support sheet comprises at least one region which approximates an ideal white and at least one region which approximates an ideal black for a range of electromagnetic wavelengths.

6. A method according to claim 1, wherein the support sheet comprises at least one region which is highly conductive to electricity, and at least one region which is essentially non-conductive.

7. A method according to claim 1, wherein the excitation stimulus is electromagnetic radiation in the ultra-violet, visible, infra-red, or micro-wave ranges.

8. A method according to claim 7, wherein the measurement of electromagnetic radiation is made at each of plural wavelengths.

9. A method according to claim 7, wherein the measurement of electromagnetic radiation is made at each of plural planes of polarization, using an excitation stimulus of polarized electromagnetic radiation in which the plane of polarization is varied.

10. A method according to claim 7, wherein the measurement of electromagnetic radiation is made at each of plural planes of polarization, using a detector of polarized electromagnetic radiation in which the plane of polarization is varied.

11. A method according to claim 7, wherein the measurement of electromagnetic radiation is made at each of plural planes of polarization, using an excitation stimulus of polarized electromagnetic radiation in which the plane of polarization is varied, and using a detector of polarized electromagnetic radiation in which the plane of polarization is varied.

12. An apparatus for measuring properties of a moving web, the apparatus comprising at least one excitation element for producing a stimulus and directing it on the web and at least one detection element for detecting the stimulus transformed by the web and at least one moving measurement support sheet which is arranged to support the web at the measuring point, the measurement support sheet comprising at least two regions having different but known responsiveness to one or more forms of stimulus or causing different but known transformation to one or more forms of stimulus.

13. An apparatus according to claim 12, wherein the measurement support sheet comprises at least one region that is essentially completely absorptive or otherwise essentially non-reflective to the excitation stimulus.

14. An apparatus according to claim 12, wherein the measurement support sheet comprises at least one region that is essentially non-absorptive or otherwise essentially completely reflective to the excitation stimulus.

15. An apparatus according to claim 13, wherein the measurement support sheet comprises at least one region that is essentially non-absorptive or otherwise essentially completely reflective to the excitation stimulus.

16. An apparatus according to claim 12, wherein the measurement support sheet comprises at least one region which approximates an ideal white and at least one region which approximates an ideal black for a range of electromagnetic wavelengths.

17. An apparatus according to claim 12, wherein the excitation element and detection element are arranged on the same side of the web to be measured.

18. An apparatus according to claim 12, wherein the support sheet comprises at least one region which is highly conductive to electricity, and at least one region which is essentially non-conductive.

19. An apparatus according to claim 12, wherein the excitation stimulus is electromagnetic radiation in the ultra-violet, visible, infra-red, or micro-wave ranges.

20. An apparatus according to claim 19, wherein the apparatus is arranged to make the measurement of electromagnetic radiation at each of plural wavelengths.

* * * * *